United States Patent [19]

Dickerson et al.

[11] Patent Number: 5,047,234
[45] Date of Patent: Sep. 10, 1991

[54] AIR FRESHENER COMPOSITION

[75] Inventors: Lyndel D. Dickerson, Centerville; John A. Ferguson; Donald Cashman, both of Cincinnati, all of Ohio

[73] Assignee: Drackett Company, Cincinnati, Ohio

[21] Appl. No.: 397,806

[22] Filed: Aug. 23, 1989

[51] Int. Cl.[5] .................. A61L 9/015; A61L 9/04; A61L 9/12
[52] U.S. Cl. .................. 424/76.2; 424/76.3; 424/76.4; 512/2; 512/3; 239/44
[58] Field of Search .................. 424/76.2, 76.3

[56] References Cited

U.S. PATENT DOCUMENTS

| | | | |
|---|---|---|---|
| 4,261,849 | 4/1981 | Benjaminson | 252/106 |
| 4,285,905 | 8/1981 | Feit | 422/239 |

FOREIGN PATENT DOCUMENTS

| | | | |
|---|---|---|---|
| 31485 | 7/1981 | Europe | C11D/00 |
| 164818 | 12/1985 | Europe | A61L/914 |
| 231084 | 8/1987 | Europe | A61L/901 |
| 305561 | 3/1989 | Europe | A62D |
| 2032959 | 2/1987 | Japan | 424/76.2 |

*Primary Examiner*—Thurman Page
*Assistant Examiner*—James M. Spear
*Attorney, Agent, or Firm*—Sandra Nolan; Charles Zeller

[57] ABSTRACT

The useful life—i.e., emulsion stability and weight loss control—of aqueous air freshener composition can be enhanced via the use therein of small amounts of certain inorganic metal salts.

18 Claims, 1 Drawing Sheet

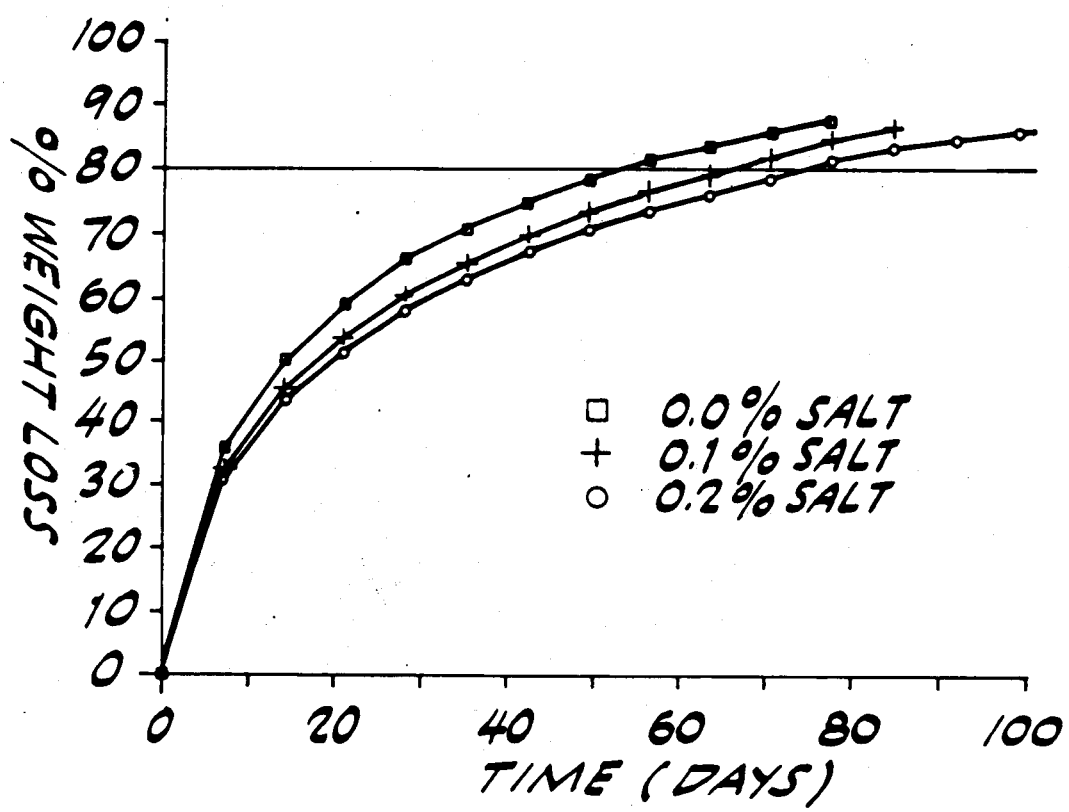
FIGURE

AIR FRESHENER COMPOSITION

BACKGROUND

Air freshener compositions containing substantial amounts of water, i.e., aqueous air fresheners, are known compositions.

Air freshening compositions may be disseminated into the environment by controlled volatilization of the composition from a reservoir via an emanating source. Any number of emanator designs may be utilized so long as sufficient surface area and pore size is maintained to permit an effective mass transport of the composition to the emanator for volatilization into the environment. In practice, the emanator serves as the metering device or rate determining mechanism step for the evaporation of the disclosed composition. As the composition volatilizes, the low volatile and/or nonvolatile materials collect on the emanator surface. Generally the evaporations rate is significantly affected when the pore volume (pore volume defined as the void area in the emanator surface) decreases below 50%. In some extreme cases, build up of nonvolatile or low volatile materials will actually clog the emanator surface and render the product nonfunctional. Thus, a desirable feature of an aqueous air freshening composition would be the maintenance of a uniform rate of volatilization over the product life.

THE INVENTION

It has been found that the addition of a small amount of an inorganic salt to an aqueous air freshener composition, which composition is disseminated into the atmosphere by a controlled volatilization from an emanator pad, lengthens the useful life of the air freshener.

In other words, applicant has found that the inclusion of 0.002 to 0.010 M of a nonvolatile, weakly solvated salt in the perfumed composition produces a more uniform evaporation rate of an effective quantity of the organoleptic perfume. This is measured by an increase in the time it takes for the total composition to volatilize from the emanator pad without losing effectiveness as an air freshener.

The inorganic additive(s) inhibit or retard weight loss, so that the evaporation rate of the freshener is slowed. In a preferred embodiment, from about 0.1 to about 0.2 wt. % of sodium chloride is added to an aqueous air freshener compositions. The resultant compositions evaporate at slower rates, so that their useful lives are extended for about one to about three weeks.

Accordingly, the invention is concerned with the methods for extending the useful life of air fresheners such as those described above and to novel compositions which employ same.

ADVANTAGES

The compositions and methods of the invention have several advantages over known formulations and methods. The compositions of the invention have significantly longer useful life due to the presence of the salts described herein.

In addition, the salts assist in inhibiting phase separation in the formulations.

Other aspects and advantages of the invention will become apparent from a consideration of the following description and claims.

DESCRIPTION OF THE INVENTION

The invention is based upon the discovery that certain inorganic salts, when added to aqueous emulsion air fresheners, produce stabilizing effects—that is, the emulsion is more stable (phase separation is inhibited) and the useful life is extended (the amount of time needed for loss of volatile fragrance components increases).

The compositions of the invention may contain eight components:
A. A salt
B. A volatile solvent
C. An emulsifier, with optional neutralizer
D. An optional co-solvent
E. A fragrance
F. Water
G. A colorant
H. Other excipients.

DRAWING

The Figure is a plot of three curves, showing percentage weight loss over a period of days using the samples and testing methods described in the Example. It could be entitled "Air Freshener Weight Loss vs. Time".

A. SALTS

The salts useful to produce the beneficial results described herein are generally inorganic metal salts. They usually contain Group IA (alkali metal) or Group II A (alkaline earth metal) cations. The preferred metals are: Li, Na, K, Be, Mg, Ca, Sr, and Be. Na and Mg are highly preferred.

The anionic portion of the salt molecules will generally be a halide, sulfate, phosphate, nitrate, carbonate or bicarbonate. Halides and sulfates are preferred.

Magnesium and sodium chloride and sodium sulfate are highly preferred. Sodium chloride is most preferred. Mixtures are operable.

B. SOLVENT

The principal solvent in the compositions of the invention contains at least one alcohol material. By "alcohol" is meant mono-hydric alkanols containing from about 2 to about 12 carbon atoms and having straight, cyclic or branched character. $C_{3-5}$ monoalcohols are preferred. Propyl alcohols are more preferred. Isopropyl alcohol is highly preferred. Mixtures are operable.

The solvent component solubilizes the fragrance and is believed to aid in controlling the formulation's evaporation.

C. EMULSIFIER

The emulsifier component is at least one of a group of phosphate ester emulsifiers. Also termed "hydroxyphosphoric acids", these compounds conform to the general formula:

$$R(OCH_2CH_2)_xOPO_3H_2$$

wherein R is an alkylphenol moiety, preferably nonylphenol, and x is an integer between about 3 and about 15, preferably about 8 to about 11.

One highly preferred material is Monafax 785 ™ a product of Mona Industries, Inc. of Paterson, N.J.) the exact formula of which is proprietary. It is believed to be a poly-(oxy-1,2-ethandiyl) alpha-nonylphenol omega-hydroxy phosphoric acid, typically referred to as a phosphate ester emulsifier (see *McCutcheon's Emulsifiers and Detergents*, North American Edition, 1984, page 198).

Monafax 786 TM (from Mona Industries) is also highly preferred. It is a nonoxynol-6 phosphate and is described at page 55 of the *CTFA Cosmetic Ingredient Dictionary*, J. M. Whelan, ed., 3rd ed. Supp. (1985)

Another commercial phosphate ester emulsifier suitable for use in this invention is available as Phosphorester 610 from the Sandoz Chemicals Corporation of Charlotte, N.C. In Sandoz bulletin #7-477/83, it is described as having exceptional solubility and as being an excellent emulsifier, even in high concentrations of alkali and salts. The manufacturer described it as a solubilizer of nonionic surfactants and as an emulsifier for aromatic and chlorinated solvents.

The emulsifier components of the inventive compositions may contain optional neutralizers, e.g., aqueous or non-aqueous base(s), to bring them to about pH 7.

D. FRAGRANCE

It is well known that the fragrant materials of air fresheners include a significant amount of one or more volatile perfume ingredient(s) in various proportions. Typically, the perfumes incorporated in the compositions used in air fresheners are mixtures of organic compounds admixed so that the combined odors of the individual components produce a pleasant or desired fragrance. While perfumes are generally mixtures of various materials, individual compounds may also be used as the perfume ingredient. Typical compounds for use, in mixtures or individually, include methyl salicylate, d-limonene and the like.

The perfume compositions generally contain several "notes," each having different volatility rates and therefore being subject to the process of chromatography which may result in a differential distribution of the notes at various times. The various notes include a main note or the "bouquet" of the perfume composition, modifiers which round off and accompany the main note, fixatives including odorous substances that lend a particular note to the perfume throughout each of the stages of evaporation, substances which retard evaporation, and top notes which are usually low-boiling, fresh-smelling materials.

Perfumery raw materials may be divided into three main groups: (1) the essential oils and products isolated from these oils; (2) products of animal origin; and (3) synthetic chemicals. Many of these materials include such substituent groups as the carbonyl group in aldehydes and ketones; the hydroxyl groups in alcohols; the acyl group in esters; the C=O groups in lactones; nitrile groups, and the oxy moiety in ethers.

The essential oils consist of complex mixtures of volatile liquid and solid chemicals found in various parts of plants. Mention may be made of oils found in flowers, e.g., jasmine, rose, mimosa, and orange blossom; flowers and leaves, e.g., lavender and rosemary; leaves and stems, e.g., geranium, patchouli, and petitgrain; barks, e.g., cinnamon; woods, e.g., sandalwood and rosewood; roots, e.g., angelica; rhizomes, e.g., ginger; fruits, e.g., orange, lemon, and bergamot; seeds, e.g., aniseed and nutmeg; and resinous exudations, e.g., myrrh. These essential oils consist of a complex mixture of chemicals, the major portion thereof being terpenes, including hydrocarbons of the formula $(C_5H_8)_n$ and their oxygenated derivatives. Hydrocarbons such as these give rise to a large number of oxygenated derivatives, e.g., alcohols and their esters, aldehydes and ketones. Some of the more important of these are geraniol, citronellol and terpineol, citral and citronellal, and camphor. Other constituents include aliphatic aldehydes and also aromatic compounds including phenols such as eugenol.

In some instances, specific compounds may be isolated from the essential oils, usually by distillation in a commercially pure state, for example, geraniol and citronellal from citronella oil; citral from lemon-grass oil; eugenol from clove oil; linalool from rosewood oil; and safrole from sassafras oil. The natural isolates may also be chemically modified as in the case of citronellal to hydroxy citronellal, citral to ionone, eugenol to vanillin, linalool to linalyl acetate, and safrol to heliotropin.

Animal products used in perfumes include musk, ambergris, civet and castoreum, and are generally provided as alcoholic tinctures.

The synthetic chemicals include not only the synthetically made and the naturally occurring isolates mentioned above, but also include their derivatives and compounds unknown in nature, e.g., isoamylsalicylate, amylcinnamic aldehyde, cyclamen aldehyde, heliotropin, ionone, phenylethyl alcohol, terpineol, undecalactone, and gamma nonyl lactone.

Perfume compositions as received from the perfumery house may be provided as an aqueous or organically solvated composition, and may include as a hydrotrope or emulsifier a surface active agent, typically an anionic or nonionic surfactant, in minor amount. The perfume compositions are quite usually proprietary blends of many different fragrance compounds to achieve a particular odoriferous effect.

Typically, perfume compositions contain an effective fragrancing amount of 0 to 100% by weight of the fragrance ingredient. Generally, perfume ingredient(s) are used in air fresheners at concentrations of about 0.01 to 75 wt. %, with solvents, emulsifiers, water, etc. making up the balance.

E. WATER

The water component used herein may be commercially available, or laboratory-prepared, deionized or demineralized water. Deionized water is preferred.

Softened water can be used. If softened water is used, the presence of the softening salts must be considered and the quantity of additional salt appropriately reduced.

In Table I, the term "q.s. to 100%" means a quantity of water sufficient to yield 100% by weight of the total composition.

F. CO-SOLVENT

The co-solvent is an optional ingredient. When used, the co-solvents are generally polyalkylene glycol monoalkyl ethers.

Dialkylene glycol monoalkyl ethers are preferred. Diethylene glycol monoethyl ether, ie., "Carbitol" is highly preferred. Mixtures can be used.

One particularly useful material of this type is the ethoxydiglycol product sold as Dowanol DE TM by Dow Chemical (Midland, Mich.) or Carbitol, Low Gravity TM, as sold by Union Carbide Corp. of Danbury, Conn. The latter compound can also be called 2-(2-ethoxyethoxy)ethanol.

This component of the composition functions as an auxiliary solubilizer and also as a volatile non-organoleptic diluent which attenuates fragrance intensity.

G. COLORANT

The colorants used in the formulations herein are commercially available dyes, preferably water soluble dyes.

Useful colorants include, but are not limited to, Azure Blue (Hilton-Davis Chemical), Erio Orange Dye (Ciba-Giegy), Rhodamine EB, and E-2GL from Sandoz Corporation. Mixtures may be used.

H. OTHER EXCIPIENTS

The air freshener compositions of the invention may contain a wide variety of excipients. Along with water, co-solvents, and other diluents, they may also contain at least one other conventional ingredient, in addition to the fragrances, colorants, neutralizers, and the like described herein. The use of fillers, thickeners, and the like, in suitable quantities appropriate to their functions, is contemplated.

AMOUNTS OF INGREDIENTS

Table I gives approximate weight percentage ranges for the ingredients used in the compositions of the invention. A skilled artisan can extrapolate from the values given in order to tailor a composition to his specific needs.

The ingredients in Section H are optional, and are not shown in Table I.

Unless otherwise stated, all percentages recited in the specification are weight percentages based on total composition weight. The terms "wt. %," "weight %," and "wt present" are used interchangeably herein.

TABLE I

| | Amounts of Ingredients WEIGHT PERCENT | | |
|---|---|---|---|
| COMPONENT | BROAD | PREFERRED | HIGHLY PREFERRED |
| Salt | 0.01–0.50 | 0.01–0.03 | 0.1–0.2 |
| Solvent (principal) | 3.0–15.0 | 7.0–10.0 | 8.0 |
| Emulsifier | 2.0–15.0 | 4.0–7.5 | 6.0 |
| Neutralizer* | 0.01–2.0 | 0.48–0.84 | 0.72 |
| Fragrance | 1.0–20.0 | 3.5–6.0 | 6.0 |
| Co-Solvent | 0–15.0 | 0–7.5 | 5.0 |
| Colorant | 0.0001–0.005 | 0.0001–0.003 | 0.0024 |
| Water | q.s. to 100% | q.s. to 100% | q.s. to 100% |

*The example shows compositions containing 50% aqueous solution of NaOH.

As used herein the phrases "suitable amount", "useful amount", "suitable quantity", and the like refer to amounts of an ingredient which are appropriate to its function in the final composition. Thus, a "suitable stabilizing quantity" or "stabilizing amount" of a salt would be an amount sufficient to produce the stabilizing effects, i.e., inhibition of phase separation and/or extension of the useful life of the air freshener via decrease of the rate of evaporation.

EXAMPLES

The following example illustrates the invention.
Preparation of formula:

Monafax 785, ispropyl alcohol, and fragrance oil are mixed until a clear solution is obtained. The water is added to this solution slowly with stirring. This results in a clear microemulsion. Dowanol DE (cosolvent) is then added with stirring followed by the sodium chloride. The following formulae were prepared.

Each of these formulations is the same except for the quantity of sodium chloride and water. Levels of sodium chloride shown here are 0.0, 0.1 and 0.2% respectively.

| RAW MATERIAL | % WEIGHT |
|---|---|
| FORMULATION A | |
| Deionized Water | 76.279 |
| Isopopropyl Alcohol | 8.000 |
| Dowanol DE | 5.000 |
| Monafax 785 | 6.000 |
| Fragrance Oil | 4.000 |
| NaOH (50% solution) | 0.720 |
| NaCl | 0.000 |
| Dye (Sandoz E-2GL) | 0.001 |
| | 100.000 |
| FORMULATION B | |
| Deionized Water | 76.179 |
| Isopopropyl Alcohol | 8.000 |
| Dowanol DE | 5.000 |
| Monafax 785 | 6.000 |
| Fragrance Oil | 4.000 |
| NaOH (50% solution) | 0.720 |
| NaCl | 0.100 |
| Dye (Sandoz E-2GL) | 0.001 |
| | 100.000 |
| FORMULATION C | |
| Deionized Water | 76.079 |
| Isopopropyl Alcohol | 8.000 |
| Dowanol DE | 5.000 |
| Monafax 785 | 6.000 |
| Fragrance Oil | 4.000 |
| NaOH (50% solution) | 0.720 |
| NaCl | 0.200 |
| Dye (Sandoz E-2GL) | 0.001 |
| | 100.000 |

Five samples were prepared from each formulation and each delivery system contained 65.0 grams of formula. Each liquid samples was then placed in a container in an environment which had air flow between 8–20 linear feet/minute, temperature 72+3° F., and relative humidity of 50+10%

Samples were removed from this environment once each week and weighed on an analytical balance. The samples were weighed each week until there was no visible liquid left in the container. The percent weight loss was calculated by the following formula:

%wt. loss = 1-(fw-(ow-cw))/fw
fw = fill weight
ow = original weight of the package with formula
cw = weight at some time t (t was measured in days)

As FIG. 1 shows, the composition of the example produced significantly slower cooperation rates when 0.1% and 0.2% NaCl were added.

Table II sets out the fragrance weight loss of Formulations A–C when tested as described above. The compositions tested are the same lemon air fresheners shown in the Figure.

TABLE II

| FRAGRANCE WEIGHT LOSS, WITH TIME, OF FORMULATIONS A-C (0.0, 0.1, AND 0.2) % NaCl | | | | | | | | | | | | | | | | |
|---|---|---|---|---|---|---|---|---|---|---|---|---|---|---|---|---|
| Week | 0 | 1 | 2 | 3 | 4 | 5 | 6 | 7 | 8 | 9 | 10 | 11 | 12 | 13 | 14 | 15 |
| Day | 0 | 7 | 14 | 21 | 28 | 35 | 42 | 49 | 56 | 63 | 70 | 77 | 84 | 91 | 98 | 105 |
| 0% NaCl | 0 | 35.54 | 49.92 | 58.69 | 65.62 | 70.62 | 74.69 | 78.38 | 81.23 | 83.23 | 85.46 | 87.54 | | | | |

TABLE II-continued

FRAGRANCE WEIGHT LOSS, WITH TIME, OF FORMULATIONS A-C
(0.0, 0.1, AND 0.2) % NaCl

| | | | | | | | | | | | | | | |
|---|---|---|---|---|---|---|---|---|---|---|---|---|---|---|
| 0.1% NaCl | 0 | 32.26 | 45.38 | 53.54 | 60.21 | 65.23 | 69.44 | 73.38 | 76.56 | 78.87 | 81.54 | 84.46 | 86.31 | |
| 0.2% NaCl | 0 | 30.8 | 43.51 | 51.35 | 57.88 | 62.74 | 66.83 | 70.71 | 73.72 | 75.94 | 78.49 | 81.2 | 83.14 | 84.95 | 86.22 | 86.92 |

It should be understood that reasonable variations, modifications and improvements, may be made by those skilled in the art in the invention disclosed herein without departing from the spirit and scope thereof.

We claim:

1. An aqueous air freshener composition consisting essentially of:
    (a) about 1 to about 20 wt. % of a fragrance component,
    (b) about 2 to about 15 wt. % of an emulsifier,
    (c) about 0.01 to about 0.5 wt. % of at least one weight loss inhibitor which is an alkali metal or alkaline earth metal halide, sulfate, nirate, carbonate, bicarbonate or phosphate, and
    (d) about 3 to about 15 wt. % of a monohydric alcohol having 2 to about 12 carbon atoms.

2. The composition of claim 1 wherein the composition contains a halide or a sulfate inhibitor.

3. The composition of claim 2 wherein the alcohol is ethyl or isopropyl alcohol.

4. The composition of claim 2 further containing from about 0.0001 to about 0.005 wt. % of a colorant.

5. The composition of claim 3 wherein the stabilizing agent is sodium chloride.

6. The composition of claim 3 wherein the stabilizing agent is magnesium sulfate.

7. A method of stabilizing a hydroalcoholic air freshener composition consisting essentially of about 1 to about 20 wt. % of a fragrance component, about 3 to about 15 wt. % of a monohydric alcohol having 2 to about 12 carbon atoms and about 2 to about 15 wt. % an emulsifier against phase separation which comprises the step of adding thereto about 0.01 to about 0.5 wt. % of at least one weight loss inhibitor which is an alkali metal or alkaline earth metal halide, sulfate, nitrate, carbonate, bicarbonate or phosphate.

8. The method of claim 6 wherein a halide or a sulfate inhibitor is used.

9. The method of claim 7 wherein the halide is sodium chloride.

10. The method of claim 7 wherein the sulfate is sodium sulfate.

11. The method of claim 7 wherein the halide is magnesium chloride.

12. A method of inhibiting the weight loss of an emulsified aqueous air freshener composition, consisting essentially of about 1 to about 20 wt. % of a fragrance component, about 3 to about 14 wt. % of a monohydric alcohol having 2 to about 12 carbon atoms and about 2 to about 15 wt. % of an emulsifier, which comprises the step of adding thereto about 0.01 to about 0.5 wt. % of at least one weight loss inhibitor which is an alkali metal or alkaline earth metal halide, sulfate, nitrate, carbonate, bicarbonate, or phosphate.

13. The method of claim 12 wherein a halide or sulfate inhibitor is used.

14. The method of claim 12 wherein the halide is sodium chloride.

15. The method of claim 12 wherein the sulfate is sodium sulfate.

16. The method of claim 12 wherein the halide is magnesium chloride.

17. In an air freshener device comprising an air freshener composition containing about 1 to about 20 wt. % of a fragrance component, about 2 to about 15 wt. % of about 3 to about 15 wt. % of a monohydric alcohol having 2 to about 12 carbon atoms a reservoir for said composition, and an emanator for volatilization of said composition, the improvement comprising incorporating in the composition about 0.01 to about 0.5 wt. % of a weight loss inhibitor which is an alkali metal or alkaline earth metal halide, sulfate, nitrate, carbonate, bicarbonate or phosphate.

18. The device of claim 16 wherein the inhibitor is selected from the group consisting of sodium chloride, sodium sulfate and magnesium chloride.

* * * * *